United States Patent [19]
Zhu et al.

[11] Patent Number: 6,015,809
[45] Date of Patent: Jan. 18, 2000

[54] PHOTOCYCLIZED RAPAMYCIN

[75] Inventors: Tianmin Zhu, Monroe, N.Y.; Hyuk-Koo Lee, San Jose, Calif.

[73] Assignee: American Home Products Corporation, Madison, N.J.

[21] Appl. No.: 09/374,654

[22] Filed: Aug. 16, 1999

Related U.S. Application Data

[60] Provisional application No. 60/113,662, Aug. 17, 1998.

[51] Int. Cl.$^7$ .................. C07D 223/00; C07D 267/22; A61K 31/395; A61K 31/44
[52] U.S. Cl. .................. 514/210; 514/291; 540/204; 540/456
[58] Field of Search .................. 540/204, 456; 514/291, 210

[56] References Cited

U.S. PATENT DOCUMENTS 3,929,992  12/1975  Sehgal et al. .................. 424/122

(List continued on next page.)

FOREIGN PATENT DOCUMENTS

| | | |
|---|---|---|
| 507555A1 | 10/1992 | European Pat. Off. . |
| 525960A1 | 2/1993 | European Pat. Off. . |
| 532862A1 | 3/1993 | European Pat. Off. . |
| WO9409010 | 9/1993 | WIPO . |

OTHER PUBLICATIONS

Venzina, C., J. Antibiot. 28:721 (1975).
Sehgal, S.N., J. Antibiot. 28:727 (1975).
Baker, H. J., Antibiot. 31:539 (1978).
Martel, R.R., Can. J. Physiol. Pharmacol. 55:48 (1977).
Staruch, M.J., FASEB 3:3411 (1989).
Dumont, F.J., FASEB 3:5256 (1989).
Calne, R.Y., Lancet 1183 (1978).
Morris, R.E., Med. Sci Res. 17:877 (1989).
Baeder, W.L., Fifth Int. Conf. Inflamm. Res. Assoc. 121 (Abstract) (1990).
Meiser, B.M., J. Heart Lung Transplant. 11 (pt. 2):197 (1992).
Stepkowski, S.M., Transplantation Proc. 23:507 (1991).

*Primary Examiner*—Mukund J. Shah
*Assistant Examiner*—Bruck Kifle
*Attorney, Agent, or Firm*—Arnold S. Milowsky

[57] ABSTRACT

A compound of the structure

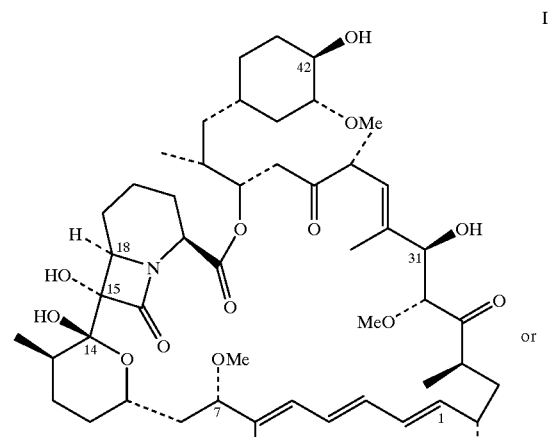

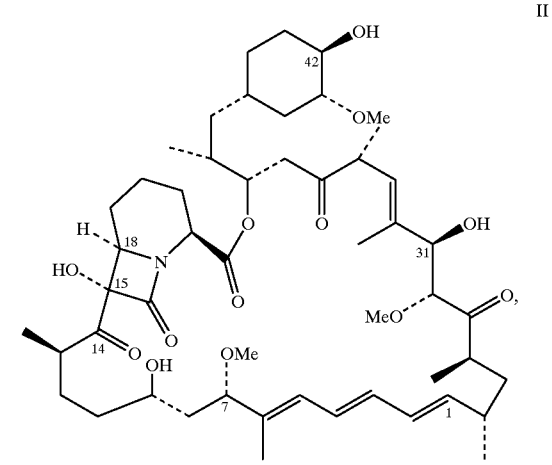

or a 31- and/or 42-ester or ether thereof, which is useful as an immunosuppressive, antiinflammatory, antifungal, antiproliferative, and antitumor agent.

4 Claims, No Drawings

U.S. PATENT DOCUMENTS

| | | | |
|---|---|---|---|
| 3,993,749 | 11/1976 | Sehgal et al. | 424/122 |
| 4,316,885 | 2/1982 | Rakhit | 424/122 |
| 4,375,464 | 3/1983 | Sehgal et al. | 424/122 |
| 4,401,653 | 8/1983 | Eng | 424/114 |
| 4,650,803 | 3/1987 | Stella et al. | 514/291 |
| 4,885,171 | 12/1989 | Surendra et al. | 424/122 |
| 5,023,262 | 6/1991 | Caufield et al. | 514/291 |
| 5,023,263 | 6/1991 | Von Burg | 514/291 |
| 5,023,264 | 6/1991 | Caufield et al. | 514/291 |
| 5,078,999 | 1/1992 | Warner et al. | 424/122 |
| 5,080,899 | 1/1992 | Sturm et al. | 424/122 |
| 5,091,389 | 2/1992 | Ondeyka et al. | 514/291 |
| 5,100,883 | 3/1992 | Schiehser | 514/183 |
| 5,100,899 | 3/1992 | Calne | 514/291 |
| 5,102,876 | 4/1992 | Caufield | 514/183 |
| 5,118,677 | 6/1992 | Caufield | 514/183 |
| 5,118,678 | 6/1992 | Kao et al. | 514/183 |
| 5,120,842 | 6/1992 | Failli et al. | 540/452 |
| 5,130,307 | 7/1992 | Failli et al. | 514/321 |
| 5,138,051 | 8/1992 | Hughes et al. | 540/456 |
| 5,151,413 | 9/1992 | Caufield et al. | 514/63 |
| 5,169,851 | 12/1992 | Hughes et al. | 514/291 |
| 5,177,203 | 1/1993 | Failli et al. | 540/456 |
| 5,194,447 | 3/1993 | Kao | 514/542 |
| 5,221,670 | 6/1993 | Caufield | 514/183 |
| 5,233,036 | 8/1993 | Hughes | 540/455 |
| 5,258,389 | 11/1993 | Goulet et al. | 514/291 |
| 5,260,300 | 11/1993 | Hu | 514/291 |
| 5,302,584 | 4/1994 | Kao et al. | 514/80 |
| 5,321,009 | 6/1994 | Baeder et al. | 514/4 |
| 5,358,944 | 10/1994 | Caufield | 514/183 |
| 5,362,718 | 11/1994 | Skotnicki et al. | 514/63 |
| 5,378,696 | 1/1995 | Caulfield | 514/183 |
| 5,385,908 | 1/1995 | Nelson et al. | 514/291 |
| 5,385,909 | 1/1995 | Nelson et al. | 514/291 |
| 5,385,910 | 1/1995 | Ocain et al. | 514/291 |
| 5,387,589 | 2/1995 | Kulkarni | 514/291 |
| 5,389,639 | 2/1995 | Failli et al. | 514/291 |
| 5,391,730 | 2/1995 | Skotnicki et al. | 540/456 |
| 5,463,048 | 10/1995 | Skotnicki et al. | 540/456 |
| 5,491,231 | 2/1996 | Nelson et al. | 540/456 |
| 5,496,832 | 3/1996 | Armstrong | 514/291 |
| 5,516,770 | 5/1996 | Waranis et al. | 514/183 |
| 5,516,781 | 5/1996 | Morris et al. | 514/291 |
| 5,563,145 | 10/1996 | Failli et al. | 514/291 |
| 5,583,139 | 12/1996 | Or et al. | 514/291 |
| 5,776,943 | 7/1998 | Christians et al. | 514/291 |
| 5,780,462 | 7/1998 | Lee et al. | 514/183 |

PHOTOCYCLIZED RAPAMYCIN

This application claims the benefit of U.S. Provisional Application No. 60/113,662, which was converted from U.S. patent application Ser. No. 09/135,421, filed Aug. 17, 1998, pursuant to a petition filed under 37 C.F.R. 1.53(c)(2)(i) on Dec. 9, 1998.

BACKGROUND OF THE INVENTION

This invention relates to photocyclized rapamycins and a method for using them for inducing immunosuppression, and in the treatment of transplantation rejection, graft vs. host disease, autoimmune diseases, diseases of inflanmmation, adult T-cell leukemia/lymphoma, solid tumors, fungal infections, and hyperproliferative vascular disorders.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. Nos. 3,929,992; and 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899].

Rapamycin has also been shown to be useful in preventing or treating systemic lupus erythematosus [U.S. Pat. No. 5,078,999], pulmonary inflammation [U.S. Pat. No. 5,080,899], insulin dependent diabetes mellitus [U.S. Pat. No. 5,321,009], smooth muscle cell proliferation and intimal thickening following vascular injury [U.S. Pat. No. 5,516,781], adult T-cell leukemia/lymphoma [European Patent Application 525,960 A1], and ocular inflammation [U.S. Pat. No. 5,387,589].

DESCRIPTION OF THE INVENTION

This invention provides photocyclized rapamycins having the structure

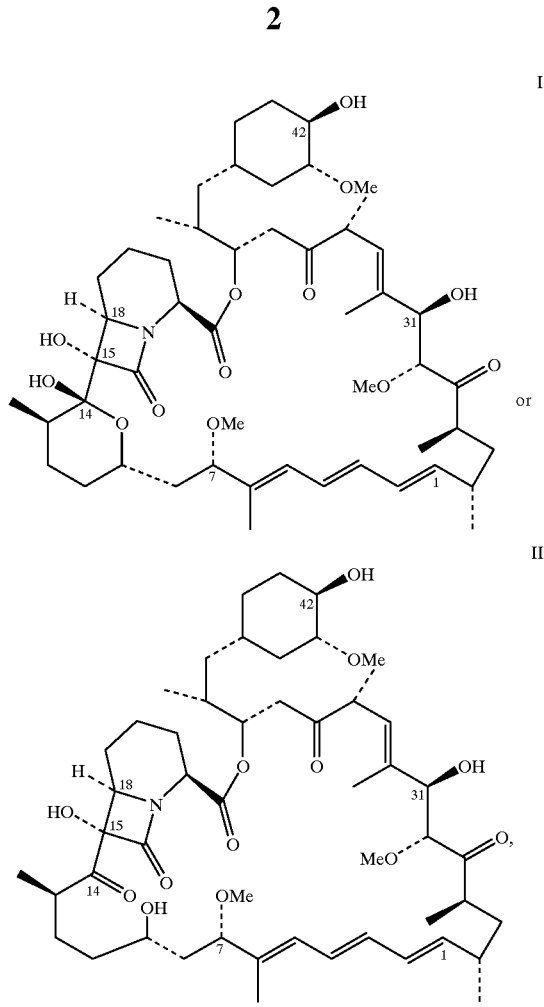

or a 31- and/or 42-ester or ether thereof.

The compounds of this invention are useful as immunosuppressive, antiinflammatory, antifungal, antiproliferative, and antitumor agents.

The β-lactam compound of formula I was prepared from by subjecting rapamycin in the solid state to a photoreaction in a sunlight cabinet for about 7 days under nitrogen. The β-lactam compound of formula II was prepared by dissolving the compound of formula I in an aqueous/organic solvent mixture, such as 1:1 tetraethylammonium acetate buffer/acetonitrile. Under the conditions described herein, the compounds of formulas I and II exist in equilibrium in solution. In the tetraethylammonium acetate buffer/acetonitrile, the equilibrium is forced towards the compound of formula II, which can be separated and isolated from the compound of formula I. The compounds of formulas I and II are also referred to as Compounds I and II, respectively.

The esters and ethers of this invention can be prepared from the compounds of Formulas I and II. Methods for preparing of 31- and/or 42-esters and ethers of rapamycin are well documented in the patent literature. The following are preferred esters and ethers, along with the corresponding patent which discloses the preparation of analogous rapamycin esters and ethers; the patents listed below are all hereby incorporated by reference: alcyl esters (U.S. Pat. No. 4,316,885); aminoalkyl esters (U.S. Pat. No. 4,650,803); fluorinated esters (U.S. Pat. No. 5,100,883); amide esters (U.S. Pat. No. 5,118,677); carbamate esters (U.S. Pat. No. 5,118,678); silyl ethers (U.S. Pat. No. 5,120,842); ami noesters (U.S. Pat. No. 5,130,307); acetals (U.S. Pat. No.

5,51,413); aminodiesters (U.S. Pat. No. 5,162,333); sulfonate and sulfate esters (U.S. Pat. No. 5,177,203); esters (U.S. Pat. No. 5,221,670); alkoxyesters (U.S. Pat. No. 5,233,036); O-aryl, -alkyl, -alkenyl, and -alkynyl ethers (U.S. Pat. No. 5,258,389); carbonate esters (U.S. Pat. No. 5,260,300); arylcarbonyl and alkoxycarbonyl carbamates (U.S. Pat. No. 5,262,423); carbamates (U.S. Pat. No. 5,302, 584); hydroxyesters (U.S. Pat. No. 5,362,718); hindered esters (U.S. Pat. No. 5,385,908); heterocyclic esters (U.S. Pat. No. 5,385,909); gem-disubstituted esters (U.S. Pat. No. 5,385,910); amino alkanoic esters (U.S. Pat. No. 5,389,639); phosphorylcarbamate esters (U.S. Pat. No. 5,391,730); carbamate esters (U.S. Pat. No. 5,411,967); carbamate esters (U.S. Pat. No. 5,434,260); amidino carbamate esters (U.S. Pat. No. 5,463,048); carbamate esters (U.S. Pat. No. 5,480, 988); carbamate esters (U.S. Pat. No. 5,480,989); carbarnate esters (U.S. Pat. No. 5,489,680); hindered N-oxide esters (U.S. Pat. No. 5,491,231); biotin esters (U.S. Pat. No. 5,504,091); and O-alkyl ethers (U.S. Pat. No. 5,665,772). When a compound of this invention is an ester or ether of Compound I or II, it is preferred that it is a 42-mono-ester or -ether.

Antifungal activity for the compounds of this invention was established by evaluating a representative compound of this invention (Compound I) against several strains of fungi. Briefly the following procedure was used to evaluate such activity. A 96 U-bottom microtiter plate was filled (50 $\mu$l/well) with RPMI 1640. The compounds to be evaluated were placed in appropriate wells, and serial diluted in successive wells to provide 11 dilutions. The concentrations ranged from 64 through 0.06 $\mu$g/ml. An adjusted inoculum of fungi (50 $\mu$l) was added to each well and the plates were incubated at 35° C. for 24–48 hours. The MIC is the lowest concentration of compound which completely inhibited growth of organism in the wells. The following table shows the results obtained in this standard pharmacological test procedure. Where the same fungi is listed more than once, it indicates that more than one strain was evaluated.

The results obtained in this standard pharmacological test procedure demonstrate that the compounds of this invention are useful as antifungal agents.

Antineoplastic activity for the compounds of this invention was established by evaluating the antineoplastic activity of a representative compound of this invention (Compound I) against six tumor cell lines in vitro. Briefly, tumor cells from six cell lines were placed in wells of a 96 well microtiter plate. The following tumor cell lines were used: A2780S (ovarian), A2780DDP (ovarian—resistant to cisplatin), A431 (vulva epidermoid origin), SW620 (colon), SKBR3 (breast), and MDA-MB-435 (breast). The tumors cells were grown in the presence of serial dilutions of the compound to be evaluated for 48 hours, and cell growth determined using a colorimetric procedure (sulforhrodamine B). The inhibition of growth was calculated compared to the number of cells at the time of test compound addition. Results are expressed as an $IC_{50}$ ($\mu$g/ml). The following $IC_{50}$s were obtained for Compound I: A2780S ($IC_{50}$=8.756 $\mu$g/ml), A2780DDP ($IC_{50}$=6.51 $\mu$g/ml), A431 ($IC_{50}$=20.46 $\mu$g/ml), SW620 ($IC_{50}$=24.84 $\mu$g/ml), SKBR3 ($IC_{50}$=7.029 $\mu$g/ml), and MDA-MB-435 ($IC_{50}$=27.28 $\mu$g/ml). The results of this standard pharmacological test procedure demonstrate that the compounds of this invention are useful as antineoplastic agents. In particular, the compounds of this invention are useful against solid tumors, including sarcomas and carcinomas; and more particularly against astrocytomas, prostate cancer, breast cancer, colon cancer, small cell lung cancer, and ovarian cancer; and adult T-cell leukemia/lymphoma.

Based on the activity profile obtained, the compounds of this invention are also useful in the treatment or inhibition of transplantation rejection such as kidney, heart, liver, lung, bone marrow, pancreas (islet cells), cornea, small bowel, and skin allografts, and heart valve xenografts; in the treatment or inhibition of graft vs. host disease; in the treatment or inhibition of autoimmune diseases such as lupus, rheumatoid arthritis, diabetes mellitus, myasthenia gravis, and mul-

TABLE I

ANTIFUNGAL ACTIVITY (MIC in $\mu$g/ml)

| Yeast/Fungi | ID | Cmpd I | Amphtericin B | Fluconazole | Miconazole | Nystatin |
|---|---|---|---|---|---|---|
| Candida albicans | 94-1 | 16 | $\leq$0.12 | $\geq$16 | 8 | 2.0 |
| Candida albicans | 1063 | 16 | 0.25 | 4 | 1 | 2 |
| Candida albicans | 1117 | 32 | 0.25 | 8 | 1 | 1 |
| Candida albicans | C-83 | $\geq$64 | 0.25 | $\geq$16 | 8 | 2 |
| Candida albicans | ATCC 90028 | 16 | 0.25 | $\geq$16 | 0.5 | 1 |
| Candida glabrata | ATCC 90030 | 8 | 0.25 | 4 | $\leq$0.12 | 1 |
| Candida parapsilosis | 94-9 | 8 | 0.5 | 0.5 | 0.5 | 1 |
| Candida parapsilosis | 94-8 | 8 | 0.25 | 0.5 | 0.25 | 1 |
| Candida parapsilosis | ATCC 90018 | 8 | $\leq$0.12 | 0.5 | $\leq$0.12 | 1 |
| Candida pseudotropicalis | ATCC 28838 | 4 | 0.25 | $\leq$0.12 | $\leq$0.12 | 1 |
| Candida tropicalis | 94-14 | 8 | 0.25 | $\geq$16 | 4 | 2 |
| Candida tropicalis | 94-13 | 16 | 0.25 | $\geq$16 | 4 | 1 |
| Candida krussii | 94-2 | $\geq$64 | 0.5 | $\geq$16 | 2 | 2 |
| Candida lusitaniae | 94-3 | 4 | $\leq$0.12 | 1 | $\leq$0.12 | I |
| Candida zeylanoided | 94-15 | 8 | 0.25 | $\geq$16 | 0.25 | 1 |
| Candida rugosa | 94-10 | 16 | 0.25 | 2 | $\leq$0.12 | 2 |
| Cryptococcus neoformans | ATCC 90112 | 8 | $\leq$0.12 | 8 | $\leq$0.12 | 0.5 |
| Filobasidiella neoformans | ATCC 7472 | $\geq$64 | 0.12 | 16 | 0.25 | 0.5 |
| Saccharomyces cerevisiae | ATCC 2601 | 8 | $\leq$0.12 | 8 | $\leq$0.12 | 2 |
| Aspergillus niger | S-430 | $\geq$64 | 0.25 | >16 | 4 | 4 |
| Aspergillus fumigatus | ATCC 26933 | $\geq$64 | 0.25 | >16 | 1 | 1 |
| Aspergillus flavus | ATCC 12963 | $\geq$64 | 2 | >16 | 0.5 | $\geq$16 | tiple sclerosis; and diseases of inflammation such as psoriasis, dermatitis, eczema, seborrhea, inflammatory bowel disease, pulmonary inflammation (including asthma, chronic obstructive pulmonary disease, emphysema, acute respiratory distress syndrome, bronchitis, and the like), and eye uveitis; and hyperproliferative vascular diseases such as restenosis and atherosclerosis. When used for restenosis, it is preferred that the compounds of this invention are used to treat restenosis that occurs following an angioplasty procedure. When used for this purpose, the compounds of this invention can be administered prior to the procedure, during the procedure, subsequent to the procedure, or any combination of the above.

When administered for the treatment or inhibition of the above disease states, the compounds of this invention can be administered to a mammal orally, parenterally, intranasally, intrabronchially, transdermally, topically, intravaginally, or rectally.

It is contemplated that when the compounds of this invention are used as an immunosuppressive or antiinflammatory agent, they can be administered in conjunction with one or more other immunoregulatory agents. Such other immunoregulatory agents include, but are not limited to azathioprine, corticosteroids, such as prednisone and methylprednisolone, cyclophosphamide, rapamycin, cyclosporin A, FK-506, OKT-3, and ATG. By combining the compounds of this invention with such other drugs or agents for inducing immunosuppression or treating inflammatory conditions, the lesser amounts of each of the agents are required to achieve the desired effect. The basis for such combination therapy was established by Stepkowski whose results showed that the use of a combination of rapamycin and cyclosporin A at subtherapeutic doses significantly prolonged heart allograft survival time. [Transplantation Proc. 23: 507 (1991)].

The compounds of this invention can be formulated neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semi-solid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

In addition, the compounds of this invention may be employed as a solution, cream, or lotion by formulation with pharmaceutically acceptable vehicles containing 0.1–5 percent, preferably 2%, of active compound which may be administered to a fungally affected area.

The dosage requirements vary with the particular compositions employed, the route of administration, the severity of the symptoms presented and the particular subject being treated. Based on the results obtained in the standard pharmacological test procedures, projected daily dosages of active compound would be 0.1 $\mu$g/kg–100 mg/kg, preferably between 0.001–25 mg/kg, and more preferably between 0.01–5 mg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The following examples illustrate the preparation and biological activities of representative compounds of this invention.

EXAMPLE 1

(1S,2R,3R,6S,8S,9E,11E,13E,15S,17R,19R,20R, 21E,23R,26S,29S,33R)-1,2,30-Trihydroxy-26-[(1R)-2-[(1S,3R,4R)4-hydroxy-3-methoxycyclohexyl]-1-methylethyl]-8,19-dimethoxy-3,9,15,17,21,23-hexamethyl-27,36-dioxa-35-azatetracyclo[27.4.2.1.[2,6].0[33,35]]hexatriaconta-9,11,13,21-tetraene-18,24,28,34-tetrone (Compound I)

Rapamycin (100 mg, 0.11 mmole each) was sealed in 10 ml ampules under nitrogen. The ampules were placed in a sunlight cabinet for 7 days. HPLC analysis showed that there was 15% of Compound I formed. The crude product was purified by preparative HPLC on a Prep Nova-pak HR C18 column (300×19 mm) using gradient method that held 60% A and 40% B for the first 5 min then changed from 60% A and 40% B to 55% A and 45% B in 30 min. Buffer A consisted of 95% 0.1 M TEAA pH 3.9 and 5% acetonitrile. Buffer B consisted of 5% 0.1 M TEAA pH 3.9 and 95% acetonitrile. The flow rate was 25 ml/min. The fraction at 28 min was collected and extracted with methylene chloride (2×50 ml). The organic layer was dried with anhydrous sodium sulfate for 4 h. The organic solvent was removed using a rotary evaporation system. The residual was dissolved in 20 mL methylene chloride and precipitated by adding 100 mL hexane. After filtration, the white solid was dried in the speed-vac overnight. The crude product was also purified by normal-phased preparative HPLC on a Prime-sphere 10 Silica (250×50 mm) column using a mobile phase consisting of 94% methylene chloride, 4% methanol and 2% isopropanol with the flow rate of 75 ml/min. The fraction from 7.6 min. was collected and the organic solvent was removed using a rotary evaporation system. From 1.87 g reaction mixture, 0.18 g of Compound I was obtained and 1.42 g rapamycin was recovered. The total conversion yield was 40%.

$^1$H NMR (DMSO-$d_6$, 400 MHz), δ 6.42 (dd, 1H, J=11.0, 14.7 Hz, H-4), 6.30 (dd, 1H, J=10.3, 14.5 Hz, H-3), 6.20 (d, 1H, J=10.8 Hz, H-5), 6.10 (dd, 1H, J=10.5, 15.2 Hz, H-2), 5.92(s, 1H, —OH at C-15), 5.45 (dd, 1H, J=9.9, 14.9 Hz, H-1), 5.32 (s, 1H, —OH at C-14), 5.20 (d, 1H, J=4.0 Hz, —OH at C-31), 5.10 (d, 1H, J=10.1 Hz, H-29), 5.04 (m, 1H, H-25), 4.56 (s, 1H), 4.21 (d, 1H, J=2.0 Hz), 4.05 (s, 1H), 3.99 (m, 1H, H-9), 3.62 (m, 3H), 3.31 (s, 3H, —OCH$_3$ at C-41), 3.19 (m, 1H), 3.17 (s, 3H, —OCH$_3$ at C-32), 3.12 (m, 3H), 3.03 (s, 3H, —OCH$_3$ at C-7), 2.82 (m, 2H), 2.52 (d, 1H, J=21.3 Hz), 2.19–2.34 (m, 4H), 2.00 (m, 1H, H-12), 1.91 (m, 2H), 1.76 (s, 3H, —CH$_3$ at C-30), 1.70 (m, 1H), 1.64 (m, 2H), 1.60 (s, 3H, —CH$_3$ at C-6), 1.53 (m, 1H), 1.38 (m, 3H), 0.97 (d, 3H, J=6.6 Hz), 0.84 (d, 3H, J=6.6 Hz), 0.80 (d, 3H, J=6.6 Hz), 0.74 (d, 3H, J=6.3 Hz), 0.61 (ddd, 1H, J=11.9 Hz, H-40a); $^{13}$C NMR data (DMSO-$d_6$ 100 MHz, δ 209.2 (C-33), 207.1 (C-27), 167.9 (C-23), 165.0 (C-16), 139.1, 138.0, 136.2, 132.4, 130.6, 127.1, 126.9, 123.8, 97.8 (C-12), 91.8 (C-15), 84.5, 83.7, 82.0, 75.7, 73.1, 72.3, 65.1, 64.8, 56.7, 56.5, 55.8, 44.3, 40.9, 35.9, 35.2, 34.7, 32.9, 32.1, 30.7, 27.2, 22.0, 21.5, 18.2 (—CH$_3$ at C-14), 15.6, 14.9, 14.7, 13.9, 12.1, 10.3.

ESI Mass Spectroscopy show a negative ion (M–H)$^-$ m/z 911.7 and positive ion (M+NH$_4$)$^+$ m/z 931. Fab Mass Spectroscopy show a m/z 913 (M), a m/z 936 (M+Na)$^+$ and a m/z 952 (M+K)$^+$, HRMS (Fab) calcd for $C_{15}H_{79}NO_{13}$ (M+Na)$^+$ 936.5449, found 936.5480.

EXAMPLE 2

(1S,4S,7R,8E,10R,11R,13R,15S,16E,18E,20E,22S, 24S,27R,29S,30R)-10,24,29-Trihydroxy-4-[(1R)-2-[(1S,3R,4R)-4-hydroxy-3-methoxycyclohexyl]-1-methylethyl]-11,22,-dimethoxy-7,9,13,15,21,27-hexamethyl-3-oxa-34-azatricyclo[27.4.2.30.34] pentatriaconta-8,16,18,20-tetraene-2,6,12,28,35-pentone (Compound II)

A solution of Compound I collected from preparative HPLC or prepared by dissolving Compound I in 50% 0.1 M TEAA buffer pH 5.7 and 50% acetonitrile was kept at room temperature overnight. HPLC analysis showed 32% of Compound II which eluted 1 min. before Compound I. The crude product was extracted with methylene chloride. The organic layer was collected and concentrated using a rotavap. The crude product was purified by preparative HPLC on a Prep Nova-pak HR C18 column (300×19 mm) using a gradient that held 60% A and 40% B for the first 5 min. then 60% A and 40% B to 55% A and 45% B in 30 min. Buffer A consisted of 95% 0.1 M TEAA pH 3.9 and 5% acetonitrile. Buffer B consisted of 5% 0.1 M TEAA pH 3.9 and 95% acetonitrile. The fraction from 25 min. was collected and extracted with methylene chloride (2×50 ml). The organic layer was dried with anhydrous sodium sulfate for 4 h. The organic solvent was removed by rotovap. The residue was dissolved in 20 ml methylene chloride and precipitated by adding 100 ml hexane. After filtering through a filter, Compound II was dried in the speedvac overnight.

$^1$H NMR (DMSO-$d_6$, 600 MHz), δ 7.19 (s, 1H, —OH at C-15), 6.45 (dd, 1H, J=11.1, 14.2 Hz, H-4), 6.2 (m, 2H, H-2, H-3), 6.05 (d, 1H, J=11.1 Hz, H-5), 5.50 (dd, 1H, J=9.2, 14.3 Hz, H-1), 5.25 (d, 1H, J=4.3 Hz, —OH at C-31), 5.1 (m, 2H, H-29, H-25), 4.58 (d, 1H, J=4.3 Hz, —OH at C-42), 4.30 (d, 1H, J=5.8 Hz, —OH at C-9), 3.90 (m, 1H, H-22), 3.85 (m, 1H, H-31), 3.79 (d, 1H, J=7.6 Hz, H-32), 3.69 (dd, 1H, J=6.7,7.0 Hz, H-7), 3.56 (m, 1H, H-28), 3.43 (dd, 1H, J=4.3, 11.3 Hz, H-18), 3.30 (s, 3H, —OCH$_3$ at C-41), 3.27 (m, 1H, H-9), 3.17 (m, 1H, H-42), 3.12 (s, 3H, —OCH$_3$ at C-32), 3.12 (m, 1H, H-12), 3.07 (s, 3H, —OCH$_3$ at C-7), 2.93 (dd, 1H, J=8.2 17.4 Hz, H-26b), 2.81 (m, 1H, H-41), 2.64 (m, 1H, H-34), 2.45 (dd,1H, J=3.8, 17.4 Hz, H-26a), 2.26 (m, 1H, H-36), 1.9 (m, 2H, H-37, H-40b), 1.72 (s, 3H, —CH$_3$ at C-30), 1.77–1.67 (m, 4H, H-11b, H-20b, H-21b, H-43b), 1.61 (s, 3H, —CH$_3$ at C-6), 1.59–1.52 (m, 3H, H-8b, H-19b, H-44b), 1.4 (m, 5H, H-8a, H-10b, H-20a, H-21a, H-35b), 1.27 (m, 1H, H-39), 1.18–1.15 (m, 3H, H-10a, H-43a, H-44a), 1.14–1.02 (m, 4H, H-11a, H-19a, H-35a, H-38a and H-38b), 1.00 (d, 3H, J=6.7 Hz, —CH$_3$ at C-36), 0.95 (d, 3H, J=6.7 Hz, —CH$_3$ at C-28), 0.93 (d, 3H, J=6.4 Hz, —CH$_3$ at C-34), 0.90 (d, 3H, J=7.0 Hz, —CH$_3$ at C-12), 0.82 (d, 3H, J=6.7 Hz, —CH$_3$ at C-37), 0.69 (ddd, 1H, J=11.9 Hz, H-40a);

$^{13}$C NMR data (DMSO-$d_6$, 100 MHz) δ 213.0 (C-33), 211.4 (C-14), 208.2 (C-27), 168.2 (C-23), 163.2 (C-16), 139.3 (C-1), 138.3 (C-30), 137.0 (C-6), 132.6 (C-3 ), 130.4 (C-2), 127.7 (C-5), 126.7 (C-4), 126.1 (C-29), 91.8 (C-15), 84.5 (C-32), 84.1 (C-7), 83.9 (C-41), 77.0 (C-31), 75.0 (C-25), 73.1 (C-42), 67.3 (C-9), 62.2 (C-18), 57.1 (—OCH$_3$ at C-32), 56.7 (—OCH$_3$ at C-41), 55.4 (—OCH$_3$ at C-7), 54.3 (C-22), 46.0 (C-28), 41.4 (C-34), 41.1 (C-8), 39.1 (C-12), 38.8 (C-26), 38.5 (C-38), 37.7 (C-35), 35.5 (C-40), 34.9 (C-36), 34.3 (C-10), 32.9 (C-43), 32.7 (C-39), 32.5

(C-37), 30.9 (C-44), 27.8 (C-11), 26.6 (C-21), 22.5 (C-19), 22.0 (—CH₃ at C-36), 19.3 (C-20), 15.3 (—CH₃ at C-12), 15.1 (—CH₃ at C-28), 14.6 (—CH₃ at C-37), 14.0 (—CH₃ at C-34), 11.8 (—CH₃ at C-30), 10.5 (—CH₃ at C-6).

ESI Mass Spectroscopy show a negative ion (M−H) m/z 912.3 and a positive ion (M+NH₄)⁺ m/z 931. Fab Mass Spectroscopy show a m/z 913 (M), a m/z 936 (M+Na)⁺ and a m/z 952 (M+K)⁺; HRMS (Fab) calcd for $C_{15}H_{79}NO_{13}$ (M+Na)⁺ 936.5449, found 936.5465.

What is claimed is:

1. A compound of the structure

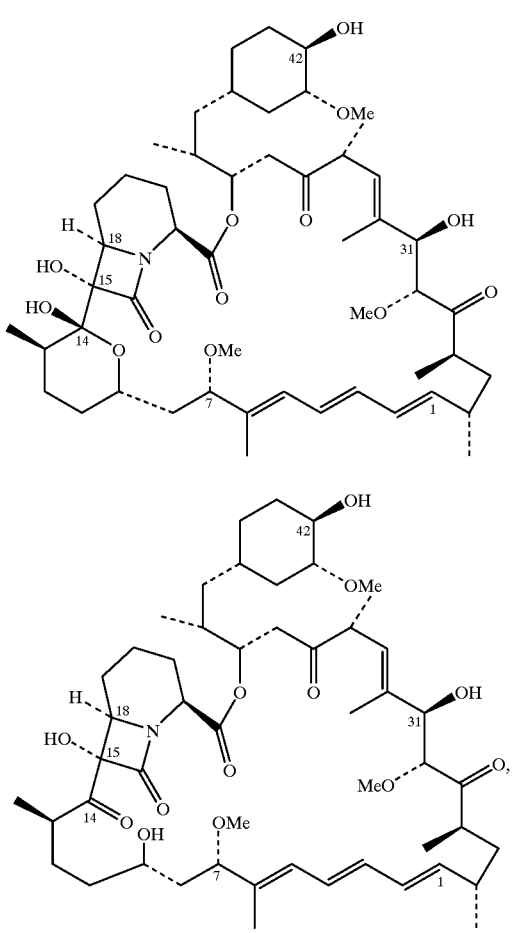

or a 31- and/or 42-ester or ether thereof.

2. The compound of claim 1, which is (1S,2R,3R,6S,8S, 9E,11E,13E,15S,17R,19R,20R,21E,23R,26S,29S,33R)-1,2, 30-Trihydroxy-26-[(1R)-2-[(1S,3R,4R)-4-hydroxy-3-methoxycyclohexyl]-1-methylethyl]-8,19-dimethoxy-3,9, 15,17,21,23-hexamethyl-27,36-dioxa-35-azatetracyclo [27.4.2.1.[2,6].0 [33,35]]hexatriaconta-9,11,13,21-tetraene-18,24,28,34-tetrone.

3. The compound of claim 1, which is (1S,4S,7R,8E,10R, 11R,13R,15S,16E,18E,20E,22S,24S,27R,29S,30R)-10,24, 29-Trihydroxy-4-[(1R)-2-[(1S,3R,4R)-4-hydroxy-3-methoxycyclohexyl]-1-methylethyl]-11,22,-dimethoxy-7,9, 13,15,21,27-hexamethyl-3-oxa-34-azatricyclo [27.4.2.30.34]pentatriaconta-8,16,18,20-tetraene-2,6,12,28, 35-pentone.

4. A pharmaceutical composition which comprises a compound of the structure

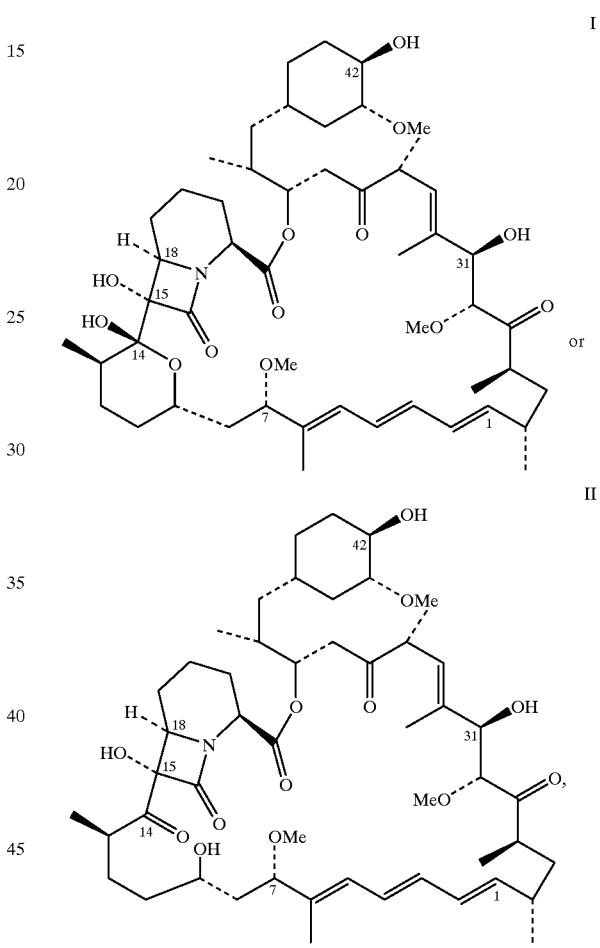

or a 31- and/or 42-ester or ether thereof and a pharmaceutical carrier.

* * * * *